United States Patent [19]

Collins et al.

[11] 4,080,386
[45] Mar. 21, 1978

[54] PRODUCTION OF ARALKYL TERTIARY HYDROPEROXIDES

[75] Inventors: Jon G. Collins, Seabrook, Tex.; David A. Hutchings, Stow, Ohio

[73] Assignee: The Goodyear Tire & Rubber Co., Akron, Ohio

[21] Appl. No.: 672,642

[22] Filed: Apr. 1, 1976

[51] Int. Cl.$^2$ ............................................ C07C 179/02
[52] U.S. Cl. .............................. 260/610 B; 260/610 A
[58] Field of Search ....................... 260/610 A, 610 B

[56] References Cited

U.S. PATENT DOCUMENTS

| 2,715,646 | 8/1955 | Hawkins | 260/610 B |
| 2,856,432 | 10/1958 | Conner et al. | 260/610 B |
| 2,856,433 | 10/1958 | Thompson | 260/610 A |
| 2,915,557 | 12/1959 | Kreps et al. | 260/610 A |
| 2,915,558 | 12/1959 | Alder et al. | 260/610 A |
| 3,190,923 | 6/1965 | Sodomann et al. | 260/610 A |
| 3,190,924 | 6/1965 | Sodomann et al. | 260/610 B |

*Primary Examiner*—James O. Thomas, Jr.
*Assistant Examiner*—Werren B. Lone
*Attorney, Agent, or Firm*—Browning, Bushman & Zamecki

[57] ABSTRACT

A portion of a recycle stream obtained as a result of the oxidation of an aryl tertiary alkane and containing aralkyl tertiary monohydroperoxide, substantial amounts of unreacted aryl tertiary alkane and lesser amounts of poly-oxy-functional oxidation by-products is subjected to aqueous alkaline extraction to remove at least a portion of the poly-oxy-functional oxidation by-products therefrom followed by separation of the extraction mixture into an aqueous alkaline phase and an organic phase, the organic phase being recycled to the oxidation reaction.

7 Claims, 1 Drawing Figure

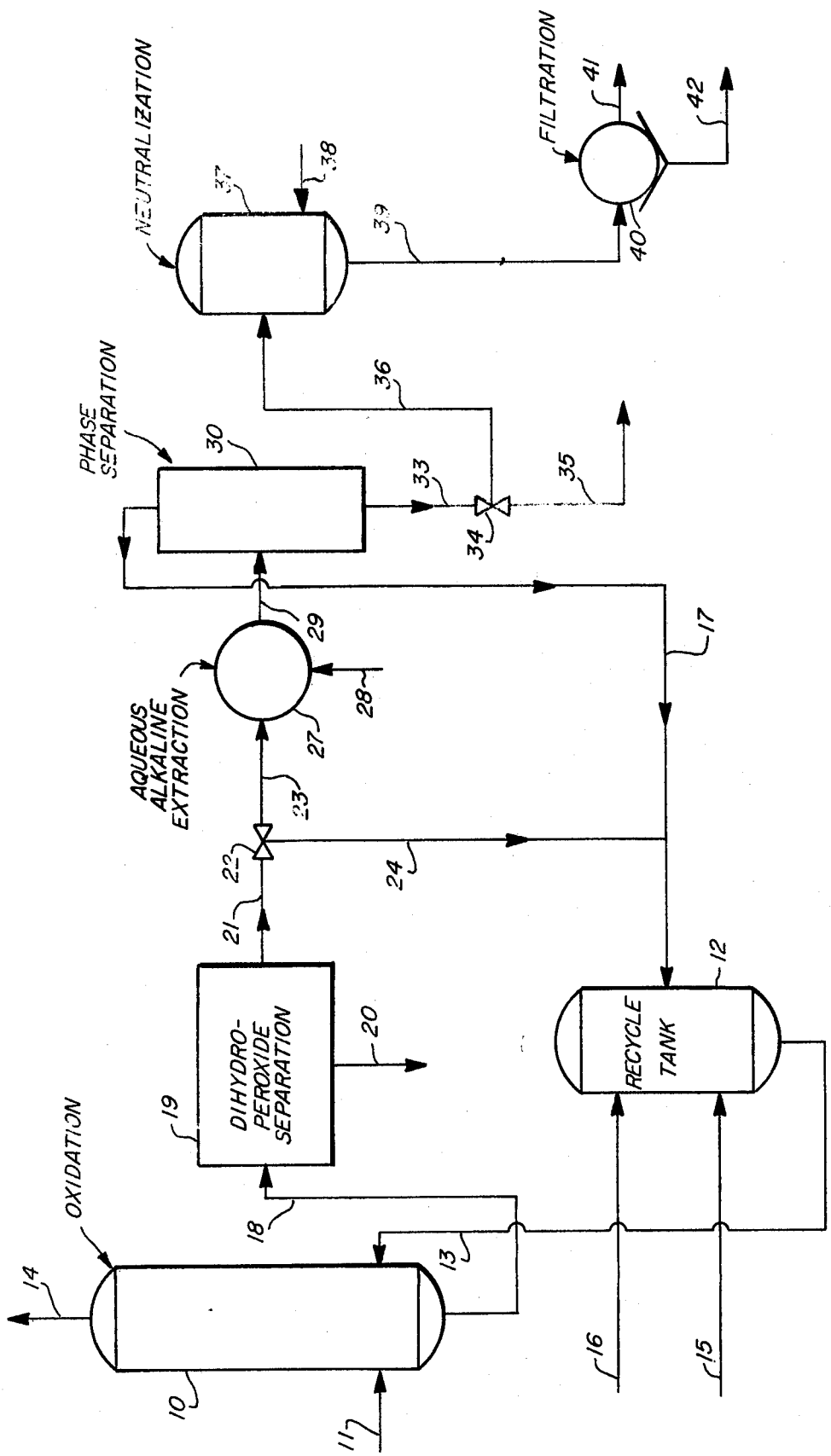

4,080,386

PRODUCTION OF ARALKYL TERTIARY HYDROPEROXIDES

BACKGROUND OF THE INVENTION

The present invention relates to the production of aralkyl tertiary hydroperoxides and more particularly to the production of p-diisopropylbenzene dihydroperoxide.

In the production of aralkyl tertiary polyhydroperoxides such as, for example, p-diisopropylbenzene dihydroperoxide, there is also produced the corresponding monohydroperoxide. Indeed, the rate of formation of the monohydroperoxide is approximately proportional to the concentration of the aryl tertiary alkane in the reaction mixture and that of the dihydroperoxide to the concentration of the monohydroperoxide. The reaction comes to a virtual standstill before all of the monohydroperoxide is converted to the dihydroperoxide and consequently for a given amount of the aryl tertiary alkane only a small proportion of the dihydroperoxide is obtained.

It is known that the oxidation reaction can be conducted so as to yield a considerably higher amount of the aralkyl tertiary dihydroperoxide if the dihydroperoxide is separated from the oxidation reaction mixture alternately or concurrently with the oxidation reaction while the oxidation is continued with the remaining reaction mixture. As a practical matter, in a continuous process the dihydroperoxide is continuously removed from the reaction mixture and the remaining portion of the oxidation reaction product is recycled to the oxidation reaction to convert the large amounts of monohydroperoxide present in the recycle stream to dihydroperoxide.

Unfortunately, the oxidation reaction product from which the dihydroperoxide has been removed and which is recycled to the oxidation reaction, in addition to containing large amounts of the monohydroperoxide and unreacted aryl tertiary alkane, also contains undesirable by-products and impurities which are quite detrimental to the efficiency of the oxidation reaction. For example, it is known that in such reactions poly-oxy-functional reaction by-products such as aralkyl tertiary dialkanols, keto aryl tertiary alkanols, etc. are also produced. As a consequence of the above-described recycle to the oxidation reactor, the poly-oxy-functional by-products continue to build up to the point where, if the oxidation reaction is to be conducted efficiently and economically, it may become necessary to completely discharge the reactor contents and charge the reactor with fresh reactants. Such a solution is both expensive and time consuming.

One method of avoiding by-product build-up in the reactor recycle loop is to purge from the system a portion of the recycle stream. Thus a fraction of the recycle stream can be evaporatively stripped to produce a light fraction containing the unreacted aryl tertiary alkane and monohydroperoxide for recycle and a heavy fraction containing the poly-oxy-functional by-products and which can be sent to waste. While such a process will control the by-product build-up such that the oxidation reaction can be conducted in a continuous manner, it results in a loss of the precursor monohydroperoxide since some of the latter remains in the heavy fraction. Thus, a process which would effectively remove deleterious amounts of the poly-oxy-functional byproducts from the reaction loop without a concomitant loss of significant amounts of monohydroperoxide is highly desirable.

SUMMARY OF THE INVENTION

It is, therefore, an object of the present invention to provide an improved process for the production of aralkyl tertiary polyhydroperoxides. Still another object of the present invention is to provide a process for treating an oxidation reaction product obtained by the oxidation of an aryl tertiary alkane with an oxygen containing gas.

A further object of the present invention is to provide a process for the oxidation of an aryl tertiary alkane to an aralkyl tertiary dihydroperoxide in which the oxidation reaction can be maintained under basically steady state conditions.

An important object of the present invention is to provide a process for the oxidation of the aryl tertiary alkane to an aryl tertiary dihydroperoxide in which poly-oxy-functional by-products are removed from the reaction recycle loop with a minimal loss of aralkyl tertiary monohydroperoxide.

These and other objects of the present invention will become apparent from the drawing, the description given herein and the appended claims.

Generally speaking, the process of the present invention comprises a novel method of treating an oxidation reaction product obtained by oxidizing an aryl tertiary alkane with an oxygen containing gas at elevated temperatures. In such a process, aralkyl tertiary polyhydroperoxide, aralkyl tertiary monohydroperoxide, mono- and poly-oxy-functional oxidation reaction by-products such as keto aryl tertiary alkanols, aralkyl tertiary dialkanols, etc. are produced. According to the process of the present invention, a portion and ideally all of the polyhydroperoxide, the desired product, and substantially all of the water, if present, is separated from the oxidation reaction product mixture leaving a substantially organic portion of the oxidation reaction mixture which can be recycled to the oxidation reaction. At least a portion of the organic recycle stream is, preferably concurrently, removed and treated with an aqueous alkaline extractant, e.g. dilute caustic, to extract at least a portion of the poly-oxy-functional oxidation reaction by-products and oxidation inhibitors such as phenols. The extraction mixture of the recycle stream and alkaline extractant is separated into aqueous alkaline and organic phases, the organic phase preferably being recycled to the oxidation reaction while the aqueous alkaline phase can be treated to recover any polyhydroperoxide.

BRIEF DESCRIPTION OF THE DRAWING

The single FIGURE is a diagrammatic representation of the process of the present invention.

DESCRIPTION OF THE PREFERRED EMBODIMENT

The process which is the subject of the present invention involves the production of aralkyl tertiary hydroperoxides obtained by the oxidation of an alkyl aromatic hydrocarbon and more specifically an aryl tertiary alkane which may contain other substituents. The term aryl tertiary alkane, as used herein, and from which the hydroperoxides are obtained is intended to include compounds defined by the formulas:

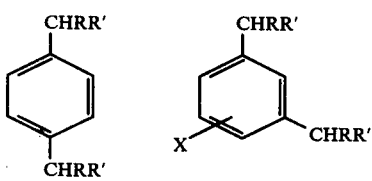

wherein R and R' may be the same or different and are alkyl or cycloaklyl and X is one of the group, hydrogen, lower alkyl, —CHRR', halogen and —NO$_2$. The alkyl radical may be straight chain or branched chain but preferably is straight chain having 1-2 carbon atoms. Non-limiting examples of such compounds include m- and p-diisopropylbenzene; m- and p-di-sec-butylbenzene; isopropyl-4-sec-butylbenzene; isopropyl-3-sec-butylbenzene; 1,3,5-triisopropylbenzene; 3,5-diisopropyltoluene; 3,5-diisopropylchlorobenzene; 3,5-diisopropylbenzene and the like. The oxidation of the above described aryl tertiary alkanes results in the formation of aralkyl tertiary hydroperoxides having the formulas:

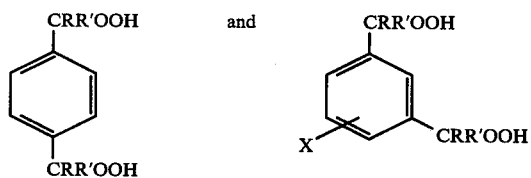

wherein R and R' have the same significance as in the previously described formulas for the aryl tertiary alkanes, but wherein X can also be —CRR'OOH as well as the above-named groupings. Non-limiting examples of such aralkyl tertiary hydroperoxides include m- and p-α,α,α',α'-tetramethyl-xylylene dihydroperoxide; m- and p-α, methyl, αethyl, α'methyl, α'-ethyl xylylene dihydroperoxide; 1, 3, 5-triisopropylbenzene dihydroperoxide; 3,5-diisopropyltoluene dihydroperoxide; 3,5-diisopropylchlorobenzene dihydroperoxide; 3,5-diisopropylnitrobenzene dihydroperoxide and the like.

The oxidation reaction is conveniently carried out in the liquid phase in the presence of an oxygen containing gas which may be pure oxygen or a gaseous mixture containing oxygen, such as air, and may with advantage include suitable proportions of ozone. It is generally preferred in the oxidation reaction to adjust the reaction parameters and the quantity of oxygen containing gas in such a way that an excess of oxygen over that absorbed by the reaction mixture is introduced therein. Such an excess may vary over wide limits but it has generally been found that an excess of at least 10% is preferred.

While not absolutely necessary, it is preferable to perform the oxidation reaction in the presence of alkaline substances such as oxides or hydroxides of the alkali and/or alkaline earth metals, or their salts with weak inorganic or organic acids such as the carbonates, bicarbonates and acetates or in the presence of other basic substances such as ammonia. The presence of the basic materials in the oxidation reaction retards the development of excessive acidity due to the formation of carboxylic acids which, in turn, hinder the oxidation reaction, or lead to a condition of spontaneous hydroperoxide decomposition.

The oxidation reaction may be conducted over a wide range of temperatures as for example from 50°-150° C. When the reaction is conducted in the homogenous phase suitable temperatures will range from between 70°-120° C and, more preferably, between 80° and 100° C at ambient pressures. Under heterogeneous conditions, as, for example, in the presence of water, temperatures between 85° and 120° C and preferably around 110° C have been found to be suitable at ambient pressure.

The oxidation reaction may be conducted at atmospheric or super-atmospheric pressure, with consequent broadening of the temperature range, or it may be conducted at sub-stmospheric pressure.

As noted, when an oxidation reaction of the type under consideration is continued for a protracted time such as occurs in a continuous process employing recycle, the rate of production of the dihydroperoxide, on the basis of a constant reaction volume, decreases progressively. This is due, in part, to the build-up in the oxidation reaction loop of by-products which are not ordinarily precursors of the dihydroperoxide. Hence their build-up effectively reduces reaction volume. The oxidation reaction by-products are generally poly-oxy-functional oxidation by-products, the exact structure of which varies depending on the nature of the aryl tertiary alkane starting material but which, in general, are compounds containing hydroxyl and/or carbonyl groups. The resulting decrease in rate of the oxidation reaction, although slow, ultimately makes it necessary to stop the oxidation and to remove, in one way or another, these by-products. Complete cessation of the reaction and recharging of the reactor is economically undesirable and consequently is to be avoided if at all possible.

In the typical process for the production of polyhydroperoxides such as dihydroperoxides, the oxidation reaction product is treated to recover the dihydroperoxide. This can be accomplished by techniques well known in the art. For example, processes for separating dihydroperoxides from the oxidation reaction mixture are disclosed in U.S. Pat. Nos. 2,856,432; 3,190,924; 2,856,433 and 3,190,923.

The recycle stream, i.e. the portion of the oxidation reaction mixture remaining after at least a portion of the polyhydroperoxide has been removed, is rich in the corresponding monohydroperoxide and unreacted aryl tertiary alkane and contains lesser amounts of the impurities noted above, i.e. poly-oxy-functional oxidation reaction by-products such as the keto aryl tertiary alkanols, the aralkyl tertiary dialkanols and the like. It is to the treatment of the recycle stream to which this process is directed.

To more fully explain the invention, reference is made to the accompanying FIGURE. While the process, as noted above, is applicable to the production of numerous aralkyl tertiary polyhydroperoxides produced from a wide variety of aryl tertiary alkanes, the invention will be described with particular reference to the production of p-diisopropylbenzene dihydroperoxide produced in the liquid phase oxidation of p-diisopropylbenzene in the presence of a dilute aqueous caustic solution. Referring then to the drawing, an oxygen containing gas, via line 11, enters reactor 10, operated at an elevated temperature. A reactor feed stream passing from recycle tank 12 via line 13 also enters reactor 10 where it is admixed with the oxygen containing gas. Gases liberated from reactor 10 are vented via line 14. The feed to recycle tank 12 comprises fresh p-diisopropylbenzene entering via line 15, a dilute caustic stream entering via line 16 and a recycle stream entering via line 17. The nature and source of the stream in the latter line will be discussed hereafter.

The oxidation reaction effluent containing unreacted p-diisopropylbenzene (p-DIPB), p-diisopropylbenzene dihydroperoxide (p-DIX), p-diisopropylbenzene monohydroperoxide (p-MOX), mono- and poly-oxy-functional oxidation reaction by-products and other impurities is removed from reactor 10 through line 18 and is sent to a dihydroperoxide recovery unit 19. As noted above, the recovery of the dihydroperoxide may be accomplished by numerous means. Preferably the recovery process is one in which substantially all water, if present, is removed along with the dihydroperoxide to leave a substantially organic recycle stream which is removed via line 21. The dihydroperoxide thus recovered is sent for further purification and processing via line 20.

The recycle stream leaving via line 21, depending upon the precise reaction conditions and when p-DIPB is employed as the starting material contains numerous components including p-DIPB, p-isopropyl acetophenone, p-MOX, 2-(4-isopropylphenyl)-2-propanol, 1,4-diacetyl benzene, 4-($\alpha$-methyl-$\alpha$-hydroxyethyl) acetophenone, p-DIX, 1($\alpha$-methyl-$\alpha$-hydroperoxyethyl)-4-($\alpha$methyl-$\alpha$-hydroxyethyl) benzene, and 1,4-Bis(1-methyl-1-hydroxyethyl) benzene.

Of the above listed compounds, those that are deemed most troublesome in terms of decreasing the oxidation reaction efficiency, if they are recycled to the oxidizer, are the di-oxy-functional oxidation reaction products which are not precursors to the dihydroperoxide and which effectively reduce reactor volume and reaction efficiency. Generally speaking, the recycle stream contains from about 5 to about 15% by-weight of the di-oxy-functional by-products.

The recycle stream in line 21 can be treated in several ways. Using a suitable valve 22, a purge stream, i.e. a portion of the stream in line 21, may be sent via line 23 to an extraction zone 27, the remaining portion of the recycle stream in line 21 returning via line 17 to recycle tank 12. It will be appreciated that by proper adjustment of valve 22, all of the stream in line 21 may be sent to extraction zone 27 if desired. In extraction zone 27, the recycle stream is extracted with an aqueous alkaline extractant, e.g. dilute caustic, entering zone 27 via line 28. The extraction mixture of the organic recycle stream and the aqueous alkaline extractant in extraction zone 27 is transferred via line 29 to phase separator 30. An organic phase containing most of the p-DIPB and p-MOX is removed from separator 30 through line 31 and passes via line 17 to recycle tank 12.

An aqueous alkaline phase containing at least some of the di-oxy-functional oxidation reaction by-products is removed from phase separator 30 through line 33. By means of a suitable valve 34, the aqueous phase may be sent through line 35 to waste as a purge stream.

Since the aqueous alkaline extractant in extraction zone 27 is effective in extracting the dihydroperoxide in the purge stream, it is generally necessary, if the process is to be operated at high efficiency, to recover the dihydroperoxide so that it can be rearranged to hydroquinone. Thus, rather than discharging the aqueous alkaline pahse from phase separator 30 to waste, it is sent via valve 34 and line 36 to neutralizer 37 where it is contacted with carbon dioxide, introduced via line 38, to adjust the pH to about 7.5 resulting in precipitation of the dihydroperoxide. The neturalized effluent leaves neutralizer 37 via line 39 and enters filter 40 where the solid dihydroperoxide is separated and recovered via line 41, the filtrate passing via line 42 to waste.

The aqueous alkaline extractant used to extract the organic recycle stream can be made from any alkaline earth or alkali metal hydroxide. Particularly preferred are alkali metal hydroxide solutions, especially sodium hydroxide solution.

The amount of aqueous alkaline extractant employed will usually be such that the weight ratio of the aqueous extractant to the portion of the recycle stream extracted is from about 0.1:1 to about 10:1. Higher ratios can be employed if desired and would probably be used in a continuous extraction technique such as countercurrent extraction.

Temperatures employed in the aqueous alkaline extraction zone can range from 0° to 100° C, temperatures from 0° to 50° C being preferred. It has been observed that lower temperatures, i.e. 0° to 50° C, give improved extraction yields and selectivity of extraction of the di-oxy-functional compounds.

In the aqueous alkaline extraction step, virtually any type of liquid-liquid extraction apparatus or technique can be employed. It has been found that more rapid phase separation occurs if mild mixing is employed. Such mixing minimizes emulsion formation. However, extraction recoveries are equivalent whether or not emulsions are formed during the extraction step. If a degree of mixing is employed in the aqueous extraction step which does not result in emulsification of the extraction mixture, phase separation times of less than 5 minutes are obtained, even for low temperature extractions, i.e. 0° – 50° C.

The aqueous alkaline extraction, in addition to removing a large portion of the objectionable di-oxy-functional oxidation reaction by-products, also removes the product dihydroperoxide from the organic recycle stream. Accordingly, if the process is to be conducted with maximum efficiency and minimum loss of the dihydroperoxide, it is desirable to recover the dihydroperoxide from the aqueous alkaline phase separated from the extraction mixture. This can be conveniently done by neutralizing the aqueous alkaline phase roughly to a pH of about 7 to 8. While neutralization can be carried out with mineral acids such as HCl, neutralization with $CO_2$ is preferred. The use of $CO_2$ as a neutralizing agent permits careful control of the pH and hence minimizes the possibility that the pH level will drop to a point where rearrangement of the dihydroperoxide will occur. Additionally, pH control can be maintained more easily using $CO_2$ because of the inherent carbonate-bicarbonate buffering system.

Neutralization of the aqueous alkaline extractant converts the disodium salt of the dihydroperoxide to the free-dihydroperoxide which precipitates out of the neutralized aqueous phase. The solid dihydroperoxide can be easily recovered by any solid-liquid separation technique such as filtration, centrifugation, etc. The recovered solid dihydroperoxide can then be rearranged to the end product, e.g. hydroquinone, the filtrate being discarded as a waste stream.

To more fully illustrate the invention, the following non-limiting examples are presented. In the examples, all composition analyses are obtained using liquid elution chromatography.

EXAMPLE 1

The recycle stream used was obtained from an oxidation reaction product mixture resulting from the oxidation of p-DIPB in an aqueous caustic solution, in the presence of oxygen, at a temperature of about 110° C. The oxidation reaction mixture was treated to remove the p-DIX, substantially all of the water and the light aromatic compounds such as benzene. A 150 cc sample of the recycle stream was extracted using 25 cc of a 2% by weight aqueous sodium hydroxide solution at about 90° C. Following the extraction, the extraction mixture was separated into an aqueous phase and an organic phase. The aqueous phase was neutralized to a pH of 7.5 to 8.0 using $CO_2$. A white solid separated on neutralization. The neutralized solution was extracted twice with 10 cc portions of diethyl ether. The ether was removed via evaporation and the remaining material from each ether extraction analyzed to determine the component distribution. The extracted aqueous solution was further acidified with 5 cc of 10 wt.% HCl. The HCl acidified solution was extracted with 10 cc of ether. The ether was evaporated and the residue weighed and analyzed. Using the results of the analyses, the weight ratio of the di-oxy-functional by-products to the p-MOX in the extract was calculated. The results are shown in Table I below. Also shown in Table I are corresponding values for the recycle stream and a typical bottoms fraction obtained by subjecting a slip stream of the recycle stream to evaporative-steam stripping to recover the p-DIPB and p-MOX as an overhead fraction for recycle to the oxidizer.

Table I

| | Wt. Ratio of Di-Oxy-Functional By-Products to p-MOX |
|---|---|
| Caustic Extract | 7.93 |
| Recycle Stream | 0.16 |
| Stripper Bottoms | 0.33 |

EXAMPLE 2

To determine the effect of the concentration of the aqueous alkaline extractant on the extraction efficiency, a series of runs were conducted using caustic solutions of varying strength. The procedure followed was identical to that set forth in Example 1. The data are presented in Table II below.

Table II

| Caustic Conc. Wt. % | Wt. Ratio of Di-Oxy-Functional By-Products to p-MOX |
|---|---|
| 0.25 | 9.1 |
| 1.00 | 5.3 |
| 2.00 | 7.9 |

As can be seen from the results in Tables I and II, the use of the aqueous alkaline extraction technique to remove unwanted impurities from the oxidizer recycle loop is more effective at purging the di-oxy-functional components than the evaporative-steam stripping technique. Additionally, and of great importance from an economic point of view, is the fact that much less of the valuable precursor monohydroperoxide is lost by using the aqueous alkaline technique. An additional advantage to the use of the aqueous alkaline extraction technique lies in the fact that acidic and phenolic impurities are also removed from the oxidizer recycle loop. Such impurities are known to inhibit the oxidation reaction and hence their removal from the recycle stream is quite desirable. Using the process, steady state conditions in the oxidizer can be maintained by preventing a build-up in the reactor recycle loop of impurities which would, if they reached sufficient levels, effectively kill the oxidation reaction.

Although the invention has been described with a certain degree of particularity, it is to be understood that such description has been made by way of example, and that numerous changes in the details of the process disclosed may be resorted to without departing from the spirit and scope of the invention as hereinafter claimed.

We claim:

1. In a process for the production of an aralkyl tertiary polyhydroperoxide having the formulas:

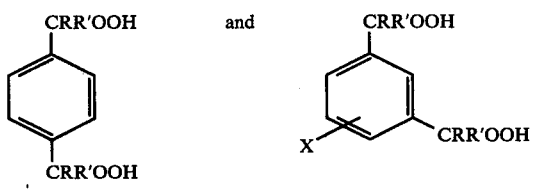

wherein R and R' may be the same or different and are alkyl groups having from 1 to 4 carbon atoms and X is one of the group, hydrogen, lower alkyl, —CHRR', —CRR'OOH, halogen and —$NO_2$, by the oxidation of an aryl tertiary alkane having the formulas:

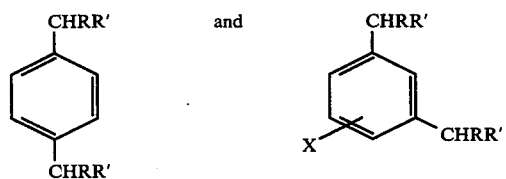

wherein R and R' may be the same or different and are alkyl groups having from 1 to 4 carbon atoms and X is one of the group, hydrogen, lower alkyl, —CHRR', halogen and —$NO_2$, with an oxygen-containing gas wherein there are produced, in addition to said aralkyl tertiary polyhydroperoxide, aralkyl tertiary monohydroperoxide and poly-oxy-functional oxidation by-products, and wherein at least a portion of said polyhydroperoxide is separated from the oxidation reaction product to produce a resultant, substantially organic recycle stream containing unreacted aralkyl tertiary alkane and aralkyl tertiary monohydroperoxide which is returned to the oxidation reaction, the improvement comprising:

(a) treating, at a temperature from about 0° to about 100° C, at least a portion of said recycle stream with an aqueous alkaline extractant comprising an aqueous solution of a compound selected from the class consisting of alkaline earth and alkali metal hydroxides to extract at least a portion of said poly-oxy-functional oxidation by-products and produce a first extraction mixture, the weight ratio of said aqueous alkaline extractant to said portion of said recycle stream being from about 0.1:1 to about 10:1, (b) separating said first extraction mixture into an aqueous alkaline phase and an organic phase, said organic phase containing the greater part of said aryl tertiary alkane present in said portion of said recycle stream, and (c) treating said alkaline phase to recover polyhydroperoxide therefrom.

2. The process of claim 1 wherein said organic phase is recycled to said oxidation reaction.

3. The process of claim 1 wherein said aqueous alkaline phase is neutralized to precipitate said polyhydroperoxide and said precipitated polyhydroperoxide is recovered by a solid-liquid separation technique.

4. The process of claim 3 wherein the neutralization is carried out using carbon dioxide.

5. The process of claim 1 wherein said aqueous alkaline extractant is an aqueous solution of sodium hydroxide.

6. The process of claim 1 wherein said alkaline material is present in said aqueous alkaline extractant in an amount of from about 0.1 to about 10% by-weight.

7. The process of claim 1 wherein said aryl tertiary alkane comprises p-diisopropylbenzene, said aralkyl tertiary polyhydroperoxide comprises p-diisopropylbenzene dihydroperoxide, and said aralkyl tertiary monohydroperoxide comprises p-diisopropylbenzene monohydroperoxide.

* * * * *